United States Patent
Cizdziel et al.

(10) Patent No.: US 6,753,187 B2
(45) Date of Patent: Jun. 22, 2004

(54) OPTICAL COMPONENT BASED TEMPERATURE MEASUREMENT IN ANALYTE DETECTION DEVICES

(75) Inventors: Phillip Cizdziel, San Jose, CA (US); Borzu Sohrab, Los Altos, CA (US); Anthony Yung, Saratoga, CA (US)

(73) Assignee: LifeScan, Inc., Milpitas, CA (US)

( * ) Notice: Subject to any disclaimer, the term of this patent is extended or adjusted under 35 U.S.C. 154(b) by 5 days.

(21) Appl. No.: 09/851,753

(22) Filed: May 9, 2001

(65) Prior Publication Data

US 2002/0168776 A1 Nov. 14, 2002

(51) Int. Cl.[7] .............................................. G01N 33/48
(52) U.S. Cl. ........................ 436/169; 436/164; 422/58; 422/61; 422/82.05; 422/82.12
(58) Field of Search ...................... 422/56, 58, 61, 422/82.05, 82.06, 82.12; 936/164, 169

(56) References Cited

U.S. PATENT DOCUMENTS

| | | | |
|---|---|---|---|
| 3,686,517 A | 8/1972 | Sexton, Jr. ................... | 307/310 |
| 4,529,949 A | 7/1985 | de Wit et al. ............... | 330/289 |
| 4,552,458 A | 11/1985 | Lowne ........................ | 356/446 |
| 4,632,559 A | 12/1986 | Brunsting ................... | 356/416 |
| 4,787,398 A | 11/1988 | Garcia et al. ............... | 128/770 |
| 4,985,205 A | 1/1991 | Fritsche et al. .............. | 422/56 |
| 5,039,225 A | 8/1991 | Uekusa ........................ | 356/448 |
| 5,049,487 A | 9/1991 | Phillips et al. ................ | 435/4 |
| 5,059,394 A | 10/1991 | Phillips et al. ............. | 422/68.1 |
| 5,477,853 A | 12/1995 | Farkas et al. ................ | 128/633 |
| 5,843,692 A | * 12/1998 | Phillips et al. ................ | 435/14 |
| 5,968,760 A | 10/1999 | Phillips et al. ................ | 435/14 |
| 5,995,236 A | * 11/1999 | Roth et al. ................... | 356/445 |

FOREIGN PATENT DOCUMENTS

| WO | WO 99/23479 | 5/1999 |
|---|---|---|

* cited by examiner

*Primary Examiner*—Lyle A. Alexander
(74) *Attorney, Agent, or Firm*—Carol M. LaSalle; Bozicevic, Field & Francis, LLP

(57) ABSTRACT

Reflectance based methods and devices are provided for determining the concentration of an analyte in a fluid sample. In practicing the subject methods, a fluid sample is applied to a matrix impregnated with a signal producing system. The signal producing system produces a detectable product in an amount proportional to the amount of analyte in the sample. A surface of the matrix is then illuminated and a reflectance measurement is obtained therefrom, generally following a predetermined incubation period. An optical component, preferably the illumination or light detection means, is also employed to obtain a temperature value corresponding to the ambient temperature of the matrix. The analyte concentration of the sample is then obtained from the reflectance measurement using an algorithm that employs the optical component derived temperature value. The subject methods and devices are suited for use in the detection of a variety of different types of fluid analytes, and are particularly suited for use in detecting the concentration of glucose in whole blood.

20 Claims, 2 Drawing Sheets

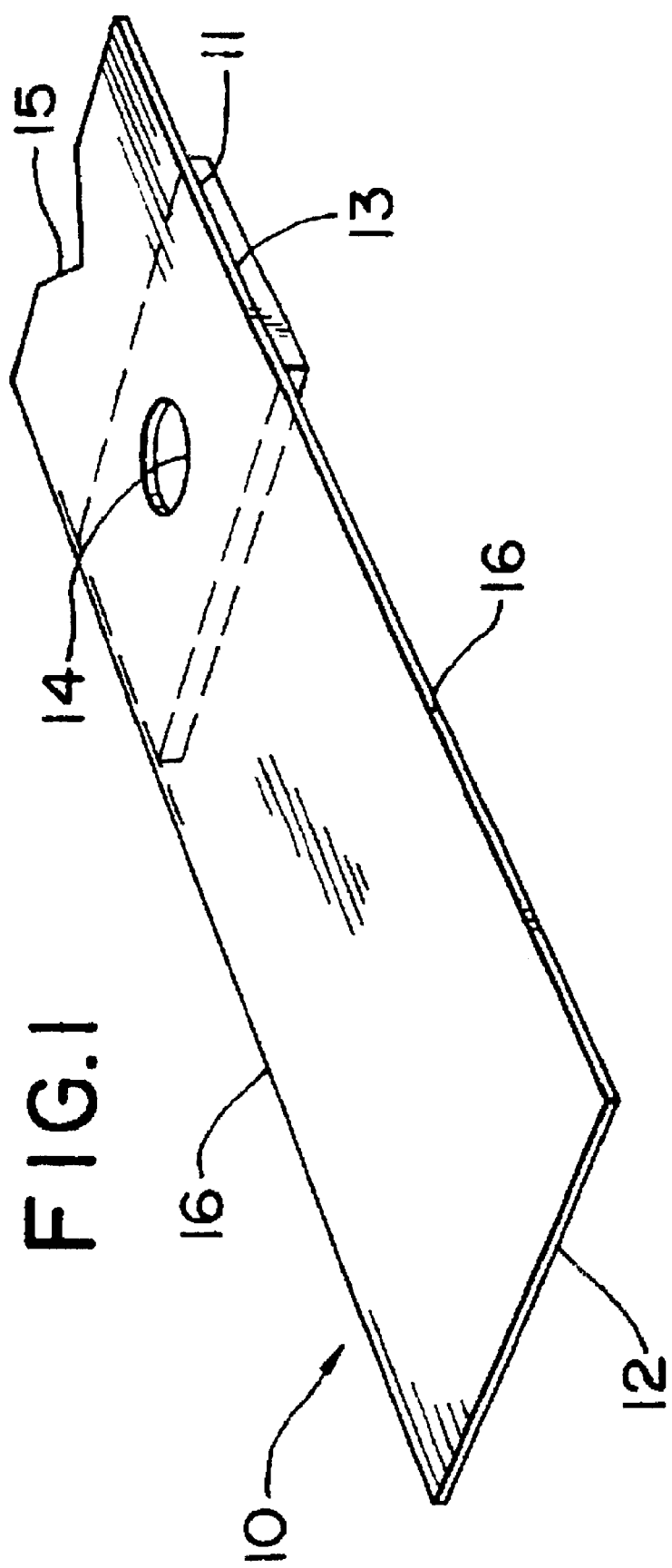

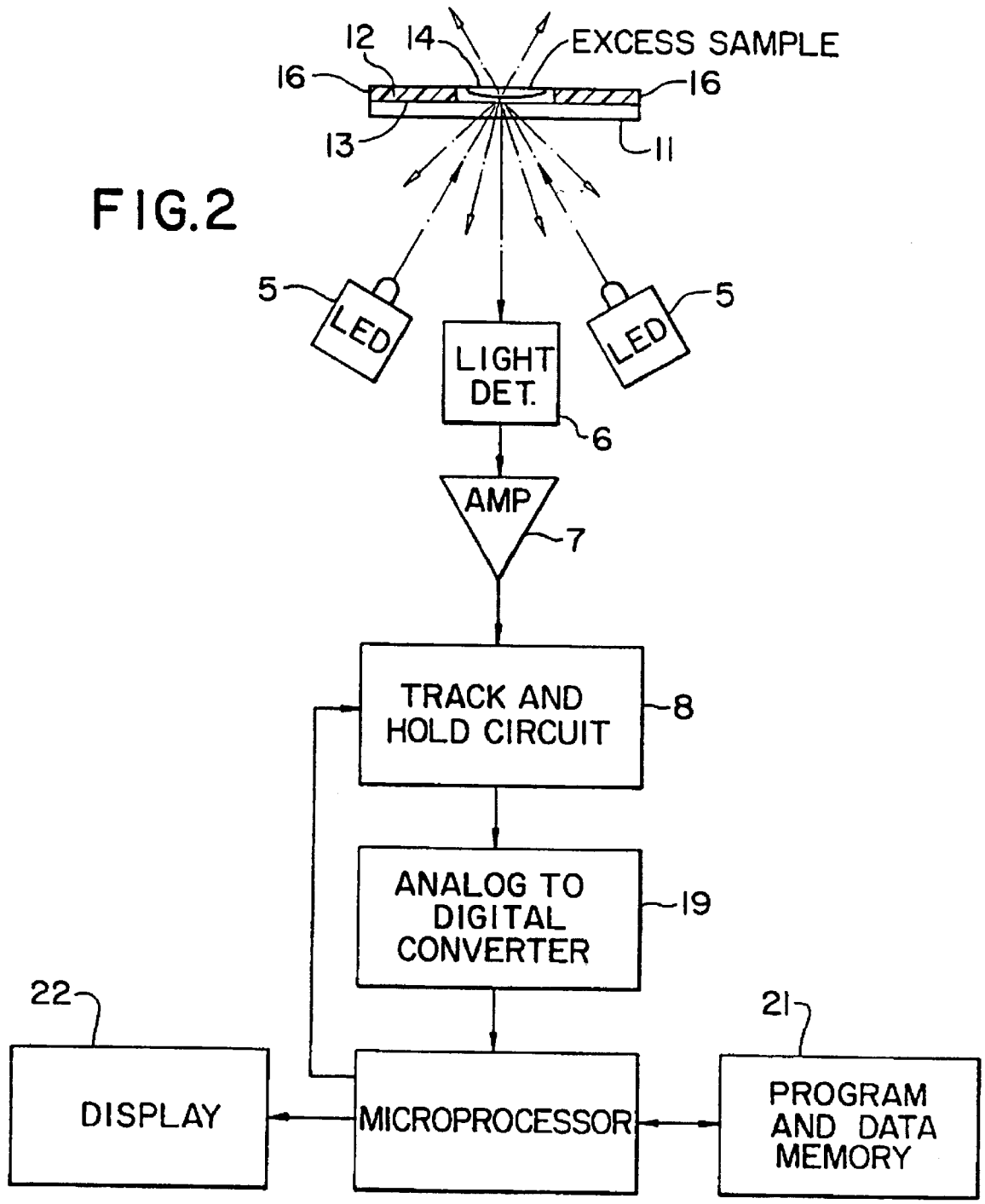

OPTICAL COMPONENT BASED TEMPERATURE MEASUREMENT IN ANALYTE DETECTION DEVICES

FIELD OF THE INVENTION

The field of this invention is fluid analyte concentration determination, particularly optical based protocols, e.g., reflectance or transmission measurement based analyte concentration determination.

BACKGROUND OF THE INVENTION

Analyte measurement in physiological fluids, e.g., blood or blood derived products, is of ever increasing importance to today's society. Analyte detection assays find use in a variety of applications, including clinical laboratory testing, home testing, etc., where the results of such testing play a prominent role in diagnosis and management in a variety of disease conditions. Analytes of interest include alcohol, formaldehyde, glucose, glutamic acid, glycerol, beta-hydroxybutyrate, L-lactate, leucine, malic acid, pyruvic acid, steroids, etc.

In response to this growing importance of analyte measurement, a variety of analyte measurement devices for enabling patients to test their own blood for the presence and concentration determination of a variety of different analytes are well known in the art. Of great interest and use in this area are optical based measurement devices in which a sample is illuminated and reflected light therefrom is detected to obtain an analyte concentration.

One such device is shown in U.S. Pat. No. 4,552,458, to Lowne, which deals with a compact reflectometer to enable the exposure of a reagent to different light beams, one red and one green. The light beams are folded by a reflecting surface, which redirects the beams through a transparent glass plate onto a reagent strip. Light is reflected back from the strip along a similar folded path onto a detector located in the same plane as the light sources.

Other patents describing various optical arrangements for illuminating and detecting the light reflected from reagent strips are U.S. Pat. No. 4,632,559, to Miles, for an optical read head for measuring non-specular, i.e., non-mirror-like, reflections from a reagent test strip; U.S. Pat. No. 4,787,398, to Garcia, for a glucose medical monitoring system and U.S. Pat. No. 4,985,205 for a test carrier analysis system. The latter '205 patent describes a reference measurement using the same optical elements by using the same reference layer so as to avoid a two tier testing process. The reference measurement uses two LED's for illuminating the same color formation layer from different directions. The LED's are preferably activated successively so that the measurements can then be averaged.

U.S. Pat. No. 5,039,225 describes a device for measuring optical density with a light transmissive plate inserted between the light source and the surface being measured. The light is directed at an angle relative to a surface of the plate so that a portion is reflected back to a detector for obtaining a reference measurement while another detector is oriented to detect diffuse light for analysis.

A characteristic of methods and devices that provide for glucose determination using a measured reflectance value is that temperature can have an impact on the final measurement, as both the optical components and chemistry are temperature sensitive. For example, light output from light emitting diodes modulates in response to ambient temperature changes. Various attempts have been made to correct for this temperature effect in reflectance measurement instruments. For example, in U.S. Pat. No. 5,995,236 and WO 99/23479, control loops are employed which measure a change in temperature and modulate the current to the light emitting diode to therefore provide for a constant output from the diode. See also U.S. Pat. No. 5,843,692 where a similar approach is employed to compensate for the temperature sensitivity of the light emitting diode.

Despite the above assay devices and protocols that have been developed, there is a continued need for further innovation in the field of optical, e.g., reflectance, measurement devices for analyte concentration determination. Of particular interest would be the development of a device that is able to accurately provide a temperature corrected analyte concentration value without the use of additional temperature sensing components, e.g., thermistors, additional diodes or detectors above those required for reflectance measurement, etc. Of particular interest would be the development of a device and method in which the power supplied to the illumination means is not modulated to compensate for temperature sensitivity.

Relevant Literature

U.S. Patents of interest include: U.S. Pat. Nos. 3,686,517; 4,529,949; 4,552,458; 4,632,559; 4,787,398; 4,985,205; 5,039,225; 5,049,487; 5,059,394; 5,477,853; 5,843,692; 5,995,236; 5,968,760. Also of interest is WO 99/23479.

SUMMARY OF THE INVENTION

Optical based methods and devices are provided for determining the concentration of an analyte in a fluid sample. In practicing the subject methods, a fluid sample is applied to a matrix impregnated with a signal producing system. The signal producing system produces a detectable product in an amount proportional to the amount of analyte in the sample. A surface of the matrix is then illuminated and an optical, e.g., reflectance, measurement is obtained therefrom, generally following a predetermined incubation period. An optical component, preferably the illumination or light detection means, is also employed to obtain a temperature value corresponding to the ambient temperature of the matrix. The analyte concentration of the sample is then obtained from the optical measurement using an algorithm that employs the optical component derived temperature value. The subject methods and devices are suited for use in the detection of a variety of different types of fluid analytes, and are particularly suited for use in detecting the concentration of glucose in whole blood.

BRIEF DESCRIPTION OF THE FIGURES

FIG. 1 is a perspective view of one embodiment of a test strip containing the reaction pad or matrix to which the fluid being analyzed is applied.

FIG. 2 is a block diagram schematic of an apparatus that can be employed in the practice of the invention.

DESCRIPTION OF THE SPECIFIC EMBODIMENTS

Optical based methods and devices are provided for determining the concentration of an analyte in a fluid sample. In practicing the subject methods, a fluid sample is applied to a matrix impregnated with a signal producing system. The signal producing system produces a detectable product in an amount proportional to the amount of analyte in the sample. A surface of the matrix is then illuminated and an optical, e.g., reflectance, measurement is obtained therefrom, generally following a predetermined incubation period. An optical component, preferably the illumination or light detection means, is also employed to obtain a temperature value corresponding to the ambient temperature of the matrix. The analyte concentration of the sample is then obtained from the optical measurement using an algorithm that employs the optical component derived temperature value. The subject methods and devices are suited for use in the detection of a variety of different types of fluid analytes, and are particularly suited for use in detecting the concentration of glucose in whole blood.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, singular references include the plural, unless the context clearly dictates otherwise. Unless defined otherwise, all technical and scientific terms used herein have the same meaning as commonly understood to one of ordinary skill in the art to which this invention belongs.

Overview

As summarized above, the subject invention is directed to optical based systems for use in detecting the concentration of an analyte of interest in a fluid sample, e.g., a body fluid sample such as whole blood or a fraction thereof. In the subject methods, a fluid sample is applied to a matrix that includes a signal producing system. The subject methods then employ an illumination and light detection means to obtain an optical measurement from which the analyte concentration is derived. A variety of optical measurements may be made and employed for analyte determination, where such measurements include reflectance measurements, transmission measurements, and the like. A feature of the invention is that an algorithm that employs a temperature value obtained using an optical component of the device, e.g., the illumination and/or detection/monitoring means, is used to derive the analyte concentration from the reflectance measurement.

In further describing the subject invention, the test strips and devices employed in the subject methods are described first in greater detail, followed by a more detailed description of the subject methods themselves.

Reagent Test Strip

The first component of the present invention to be considered is a reagent element or reagent test strip, which includes a substrate that is conveniently in the shape of a pad, made up of an inert porous matrix and the component or components (i.e., reagent(s)) of a signal producing system, which system is capable of reacting with an analyte to produce a light-absorbing reaction product. The signal producing components are impregnated into the pores of the porous matrix. The signal-producing system does not significantly impede the flow of liquid through the matrix.

In order to assist in reading reflectance, it is preferred that the matrix have at least one side which is substantially smooth and flat. Typically, the matrix is formed into a thin sheet with at least one smooth, flat side. The matrix is a hydrophilic porous matrix to which reagents are covalently or noncovalently bound. The matrix allows for the flow of an aqueous medium through the matrix. It also allows for binding of protein compositions to the matrix without significantly adversely affecting the biological activity of the protein, e.g., enzymatic activity of an enzyme. To the extent that proteins are to be covalently bound, the matrix has active sites for covalent bonding or is activated by means known to the art. The composition of the matrix is reflective and is of sufficient thickness to permit the formation of a light-absorbing dye in the void volume or on the surface to substantially affect the reflectance from the matrix. The matrix is of a uniform composition or a coating on a substrate providing the necessary structure and physical properties.

The matrix is usually not deformed on wetting, and therefore retains its original conformation and size upon wetting. The matrix has a defined absorbance, so that the volume which is absorbed can be calibrated within reasonable limits, variations usually being maintained below about 50% preferably not greater than 10%. The matrix has sufficient wet strength to allow for routine manufacture. The matrix permits noncovalently bound reagents to be relatively uniformly distributed on the surface of the matrix.

As exemplary of matrix surfaces are polyamides, particularly with samples involving whole blood. The polyamides are conveniently condensation polymers of monomers of from 4 to 8 carbon atoms, where the monomers are lactams or combinations of diamines and di-carboxylic acids. Other polymeric compositions having comparable properties may also find use. The polyamide compositions may be modified to introduce other functional groups which provide for charged structures, so that the surfaces of the matrix may be neutral, positive or negative, as well as neutral, basic or acidic. Preferred surfaces are positively charged. It has been determined that this positive charge enhances both stability and shelf-life.

When used with whole blood, the porous matrix preferably has pores with an average diameter in the range of from about 0.1 to 2.0 $\mu$m, more preferably from about 0.6 to 1.0 $\mu$m. When the porous matrix contains pores having an average diameter of about 0.8 $\mu$m, the sample of blood does not cause a chromatographic effect. That is, the blood sample does not seek out the edges of the circular matrix. Rather, the blood remains seated within all the pores of the matrix and provides for a uniform readability of the entire matrix. In addition, this pore size maximizes the non-blotting effect of the blood. That is, the pore size is both adequately filled, but not overfilled, so that the hematocrit level of blood will not cause the sample to require blotting prior to reading of the sample. Also, it has been found that pores of this size are optimal when shelf-life and stability are taken into consideration.

A preferred manner of preparing the porous material is to cast the hydrophilic polymer onto a core of non-woven fibers. The core fibers can be any fibrous material that produces the described integrity and strength, such as polyesters and polyamides. The reagent that will form the light-absorbing reaction product, which is discussed later in detail, is present within the pores of the matrix but does not block the matrix so that the liquid portion of the assay medium, e.g. blood, being analyzed can flow through the pores of the matrix, while particles, such as erythrocytes, are held at the surface.

The matrix is substantially reflective so that it gives a diffuse reflectance without the use of a reflective backing. Preferably at least 25%, more preferably at least 50%, of the incident light applied to the matrix is reflected and emitted as diffuse reflectance. A matrix of less than about 0.5 mm thickness is usually employed, with from about 0.01 mm to about 0.3 mm being preferred. A thickness of from about 0.1 mm to about 0.2 mm is most preferred, particularly for a nylon matrix.

Typically, the matrix is attached to a holder in order to give it physical form and rigidity, although this may not be necessary. FIG. 1 shows one embodiment of the invention in which there is a reagent test strip 10 having a thin hydrophilic matrix pad 11 positioned at one end of a plastic holder or handle 12 by means of an adhesive 13 which directly and firmly attaches the reagent pad 11 to the handle 12. A hole 14 is present in the plastic holder 12 in the area to which reagent pad 11 is attached so that sample can be applied to one side of the reagent pad and light reflected from the other side.

Generally, with blood being exemplary of a sample being tested, the reagent pad or matrix will be on the order of about 10 mm$^2$ to 100 mm$^2$ in surface area, especially 10 mm$^2$ to 50 mm$^2$ area (or having a diameter of about 2 mm to about 10 mm), which is normally a volume that 5–10 microliters of sample will more than saturate. Of course, once saturation is reached at above the threshold of about 5–10 microliters, no other requirement of blood amount is necessary. As can be seen from FIG. 1, the support holds reagent pad or matrix 11 so that a sample can be applied to one side of the reagent pad 11 while light reflectance is measured from the side of the reagent pad 11 opposite the location where sample is applied.

FIG. 2 shows a system in which the reagent is applied to the side with the hole 14 in the backing handle 12 while light is reflected and measured on the other side of the reagent pad 11. Other structures than the one depicted may be employed. The pad 11 may take various shapes and forms, subject to the limitations provided herein. The pad 11 will be accessible on at least one surface and usually two surfaces.

The hydrophilic layer (reagent element) may be attached to the support by any convenient means, e.g., a holder, clamp or adhesives; however, in the preferred method it is bonded to the backing. The bonding can be done with any non-reactive adhesive, by a thermal method in which the backing surface is melted enough to entrap some of the material used for the hydrophilic layer, or by microwave or ultrasonic bonding methods which likewise fuse the hydrophilic sample pads to the backing. It is important that the bonding be such as to not itself interfere substantially with the diffuse reflectance measurements or the reaction being measured, although this is unlikely to occur as no adhesive need be present at the location where the reading is taken. For example, an adhesive 13 can be applied to the backing strip 12 followed first by punching hole 14 into the combined strip and adhesive and then applying reagent pad 11 to the adhesive in the vicinity of hole 14 so that the peripheral portion of the reagent pad attaches to the backing strip.

As mentioned above, impregnated in the reagent pad or matrix is a signal producing system made up of a plurality of reagent components that produce a detectable product in the presence of the analyte of interest. The signal producing system is typically an analyte oxidation signal producing system. By analyte oxidation signal producing system is meant that in generating the detectable signal from which the analyte concentration in the sample is derived, the analyte is oxidized by a suitable enzyme to produce an oxidized form of the analyte and a corresponding or proportional amount of hydrogen peroxide. The hydrogen peroxide is then employed, in turn, to generate the detectable product from one or more indicator compounds, e.g., dye couples, where the amount of detectable product produced by the signal producing system, i.e., the signal, is then related to the amount of analyte in the initial sample. As such, the analyte oxidation signal producing systems typically present in the subject test strips are also correctly characterized as hydrogen peroxide based signal producing systems or peroxide producing signal producing systems.

As indicated above, the hydrogen peroxide based signal producing systems include an enzyme that oxidizes the analyte and produces a corresponding amount of hydrogen peroxide, where by corresponding amount is meant that the amount of hydrogen peroxide that is produced is proportional to the amount of analyte present in the sample. The specific nature of this first enzyme necessarily depends on the nature of the analyte being assayed but is generally an oxidase. As such, the enzyme may be: glucose oxidase (where the analyte is glucose); cholesterol oxidase (where the analyte is cholesterol); alcohol oxidase (where the analyte is alcohol); formaldehyde dehydrogenase (where the analyte is formaldehyde), glutamate oxidase (where the analyte is L-glutamic acid), glycerol oxidase (where the analyte is glycerol), galactose oxidase (where the analyte is galactose), a ketoamine oxidase (where the analyte is a glycated protein, e.g., fructosamine), a 3-hydroxybutyrate dehydrogenase (where the analyte is a ketone body), L-ascorbate oxidase (where the analyte is ascorbic acid), lactate oxidase (where the analyte is lactic acid), leucine oxidase (where the analyte is leucine), malate oxidase (where the analyte is malic acid), pyruvate oxidase (where the analyte is pyruvic acid), urate oxidase (where the analyte is uric acid oxidase) and the like. Other oxidizing enzymes for use with these-and other analytes of interest are known to those of skill in the art and may also be employed.

The signal producing systems also include an enzyme that catalyzes the conversion of a dye substrate into a detectable product in the presence of hydrogen peroxide, where the amount of detectable product that is produced by this reaction is proportional to the amount of hydrogen peroxide that is present. This second enzyme is generally a peroxidase, where suitable peroxidases include: horseradish peroxidase (HRP), soy peroxidase, recombinantly produced peroxidase and synthetic analogs having peroxidative activity and the like. See e.g., Ci et al. (1990) *Analytica Chimica Acta,* 233:299–302.

The dye substrates are oxidized by hydrogen peroxide in the presence of the peroxidase to produce a product that absorbs light in a predetermined wavelength range, i.e., an indicator dye. Preferably the indicator dye absorbs strongly at a wavelength different from that at which the sample or the testing reagent absorbs strongly. The oxidized form of the indicator may be the colored, faintly-colored, or colorless final product that evidences a change in color of the testing side of the membrane. That is to say, the testing reagent can indicate the presence of an analyte in a sample by a colored area being bleached or, alternatively, by a colorless area developing color. Examples of dye substrates of interest include ANS and MBTH or analogues thereof; MBTH-DMAB; AAP-CTA; and the like. See e.g., in U.S. Pat. Nos. 5,922,530; 5,776,719; 5,563,031; 5,453,360 and 4,962,040; the disclosures of which are herein incorporated by reference.

Optical Reading Device

In the subject methods, an optical reading device is employed to automatically take an optical measurement, e.g., a transmission measurement, reflectance measurement, etc., which optical measurement is employed to derive the analyte concentration in the sample. In many embodiments, a suitable instrument, such as a diffuse reflectance spectrophotometer with appropriate software, is employed to automatically read reflectance at certain points in time, calculate a rate of reflectance change, and, using calibration factors, output the level of analyte in the aqueous fluid. As explained in greater detail below, a feature of the devices of the subject invention is that they include a means for determining a temperature value representative of the ambient temperature of the matrix by using an optical component of the device, e.g., the illumination or light detection means, and then using this temperature value in the optical, e.g., reflectance, measurement analyte determination algorithm.

A representative reflectance reading device that may be employed in the subject invention is schematically shown in FIG. 2. In FIG. 2, a device of the invention is depicted where the device includes a backing 12 to which reagent pad 11 is affixed is shown. Light source 5, for example a high intensity light emitting diode (LED), projects a beam of light onto the reagent pad. A substantial portion (at least 25%, preferably at least 35%, and more preferably at least 50%, in the absence of reaction product) of this light is diffusively reflected from the reagent pad and is detected by light detector 6, for example a photodetector that produces an output current proportional to the light it receives. Light source 5 and/or detector 6 can be adapted to generate or respond to a particular wavelength of light, if desired. The output of detector 6 is passed to amplifier 7, for example, a circuit which converts the photodetector current to a voltage.

Analog-to-digital converter 19 takes the analog voltage and converts it to, for example, a twelve-bit binary digital number upon command of microprocessor 20. Microprocessor 20 can be a digital integrated circuit. It serves the following control functions: 1) timing for the entire system; 2) reading of the output of analog/digital converter 19; 3) together with program and data memory 21, storing data corresponding to the reflectance measured at specified time intervals; 4) calculating analyte levels from the stored reflectances using an algorithm that employs a temperature value obtained using an optical component of the device; and 5) outputting analyte concentration data to display 22. Memory 21 can be a digital integrated circuit which stores data and the microprocessor operating program. The algorithm is typically recorded on a computer readable medium, which is any medium capable of storing the algorithm and being read by a computing means, e.g., the processor. Reporting device 22 can take various hard copy and soft copy forms. Usually it is a visual display, such as a liquid crystal (LCD) or LED display, but it can also be a tape printer, audible signal, or the like. The instrument also can include a start-stop switch and can provide an audible or visible time output to indicate times for applying samples, taking readings etc., if desired.

In the present invention, the reflectance circuit itself can be used to initiate timing by measuring a drop in reflectance that occurs when the aqueous portion of the suspension solution applied to the reagent pad (e.g., blood) migrates to the surface at which reflectance is being measured. Typically, the measuring device is turned on in a "ready" mode in which reflectance readings are automatically made at closely spaced intervals (typically about 0.2 seconds) from the typically off-white, substantially dry, unreacted reagent strip. The initial measurement is typically made prior to penetration of the matrix by fluid being analyzed but can be made after the fluid has been applied to a location on the reagent element other than where reflectance is being measured. The reflectance value is evaluated by the microprocessor, typically by storing successive values in memory and then comparing each value with the initial unreacted value. When the aqueous solution penetrates the reagent matrix, the drop in reflectance signals the start of the measuring time interval. Drops in reflectance of 5–50% can be used to initiate timing, typically a drop of about 10%. In this simple way there is exact synchronization of assay medium reaching the surface from which measurements are taken and initiation of the sequence of readings, with no requirement of activity by the user.

Reflectance reading devices that may be adapted for use in the subject invention, e.g., by modifying the reflectance measurement based analyte concentration determination algorithms present therein to employ a temperature value obtained from the optical components, e.g., LEDs, photodetectors, of the devices, are further described in U.S. Pat. Nos. 4,734,360; 4,900,666; 4,935,346; 5,059,394; 5,304,468; 5,306,623; 5,418,142; 5,426,032; 5,515,170; 5,526,120; 5,563,042; 5,620,863; 5,753,429; 5,573,452; 5,780,304; 5,789,255; 5,843,691; 5,846,486; and the like, the disclosures of which are herein incorporated by reference.

Methods of Analyte Concentration Determination

In practicing the subject methods, the first step is to obtain the sample of aqueous fluid containing an analyte to be assayed. In many embodiments, the fluid sample is a body fluid sample, by which is meant that it is a fluid sample which is obtained from an animal, e.g., a human, or tissue thereof. Representative body samples of interest include whole blood or fractions thereof. Where the sample is blood, blood may be obtained by a finger stick or other convenient means. Following provision of the fluid sample, the fluid sample is then contacted with the reagent pad or matrix. Contact is generally achieved by applying the liquid sample being analyzed to one side of the matrix pad of the reagent test strip. An excess of this fluid over threshold matrix saturation in the area where reflectance will be measured (i.e., about 5–10 microliters) is applied to the reagent element or elements of the test device. Excess fluid can be removed, such as by light blotting, but such removal is also not required.

Following application to the matrix, any assay compound present in the sample passes through the reagent element or matrix by means of capillary, wicking, gravity flow and/or diffusion actions. The components of the signal producing system present in the matrix subsequently react to give a light absorbing reaction product.

Following application of the sample to the test strip and typically at the conclusion of a predetermined incubation time ranging from about 5 to 120, usually from about 10 to 60 seconds (which incubation time may be automatically started or manually started, depending on the nature of the device an protocol being employed), an optical measurement is obtained. In those embodiments where the optical measurement is a reflectance measurement, a surface of the matrix pad, typically that opposite the surface to which the sample was applied, is illuminated with an illumination means, e.g., an LED. The wavelength of illuminating light may range from about 300 to 3000 nm, usually from about 400 to 1000 nm, and more usually from about 600 to 750 nm, e.g., 635 nm, 700 nm, etc.

Light is thus reflected from the surface of the element as diffuse reflected light. This diffuse light is collected and measured, for example by the detector of a reflectance spectrophotometer. The amount of reflected light is then related to the amount of analyte in the sample, usually being an inverse function of the amount of analyte in the sample. In other words, absorbance is measured at certain points in time after application of the sample, i.e., at the conclusion of the incubation period. Absorbance refers in this application not only to light within the visual wavelength range but also outside the visual wavelength range, such as infrared and ultraviolet radiation. From these measurements of absorbance a rate of color development can be calibrated in terms of analyte level.

As such, a reflectance measurement is obtained at the conclusion of the predetermined incubation period. An algorithm is then employed to derive the concentration of the analyte of interest from the reflectance measurement.

As mentioned above, a feature of the subject invention is that the algorithm employed to determine analyte concentration, i.e., the reflectance measurement analyte concentration determination algorithm, is one that employs a temperature value. Importantly, the temperature value is one that is obtained from an optical component of the reflectance reading device, and more particularly a temperature sensitive optical component of the reflectance reading device, e.g., a light emitting diode or a photodetector. In many embodiments, the temperature value employed in the analyte concentration determination algorithm is one that is obtained from a temperature sensitive illumination means of the device, e.g., a light emitting diode.

The temperature value is obtained from the temperature sensitive optical component of the reflectance reading device using any convenient protocol. For example, the voltage drop across a light emitting diode of the device at a fixed current can be determined at a point in time proximal to, e.g., prior to or after, or simultaneous with, the end of the incubation period. Based on the calibration of unit, the measured voltage drop can be used to derive a temperature value representative of the ambient temperature of the matrix pad. Methods of using light emitting diodes to determine temperature of the diode are known to those of skill in the art. See e.g., WO 99/23479 and its priority U.S. Provisional Application Serial No. 60/063,935; the disclosure of the latter of these documents being incorporated herein by reference with respect to its teaching of how to employ a light emitting diode to determine ambient temperature of the diode. In the devices employed in the subject invention, the optical component employed to determine optical component temperature is sufficiently proximal to the matrix so as to substantially provide the ambient temperature of the matrix. By sufficiently proximal is meant that the distance between the optical component and the matrix generally ranges from about 0.5 mm to 25 mm, usually from about 1.0 mm to 10 mm, and more usually from about 1.5 mm to 5.5 mm. By substantially the same as the matrix is meant that the measured temperature varies, if at all, from the actual temperature of the matrix by no more than about 4° C., usually by no more than about 2° C. and more usually by no more than about 1° C.

As indicated above, the temperature value employed in the subject methods, i.e., the temperature of the diodes, may be determined using a temperature sensitive optical component of the device at any convenient point during the measurement procedure. As such, the temperature is measured at least once, and may be measured a plurality of times during the procedure, where when the temperature is measured a plurality of times, the multiple measured temperature values may be averaged to produce a single temperature value for use in the analyte concentration determination algorithm.

Following obtainment of the reflectance measurement and temperature value as described above, these two factors are employed in an analyte concentration determination algorithm to obtain an analyte concentration value for the sample. Any convenient analyte determination algorithm may be employed that is capable of converting the reflectance measurement value in conjunction with the temperature value to obtain an analyte concentration value.

The algorithm that is employed necessarily varies depending on the nature of the analyte and the signal producing system, as well as the particular reflectance reading device, that are employed. A representative algorithm that may be employed where the analyte of interest is glucose and the fluid sample is whole blood is a modified version of the algorithms described in U.S. Pat. Nos. 5,049,487; 5,059,394; 5,843,692 and 5,968,760; the disclosures of which are herein incorporated by reference. In these algorithms, one or more K/S values are obtained from the raw reflectance data, where the values are then related to analyte concentration. In the algorithms employed by the subject methods, the K/S values are employed in conjunction with the temperature value measured using an optical component of the device, e.g., the illumination means, in order to obtain the analyte concentration. A specific representative algorithm is:

Glucose $(mg/dL)$=Function of $(K/S1(t_1),K/S1(t_2), \ldots ,K/S1(t_n),K/S2(t_1),K/S2(t_2), \ldots ,K/S2(t_n),K/S3(t_1),K/S3(t_2), \ldots ,K/S3(t_n)$, Temperature)

where K/S 1 $(t_1)$=Normalized reflectance value measured at wavelength 1 and time $t_1$ It is evident from the above discussion that the invention provides for an important improvement in the field of reflectance based measurement of analyte concentration. By using the optical components to determine temperature of the illumination and/or detection means and therefore the matrix in which the detectable product is employed and then using the measured temperature value directly in the analyte concentration determination algorithm, a more accurate determination of analyte concentration can be made. In the case of optical components, such as an LED or photodiode, used for the above temperature measurement, the temperature dependent measurements are linear with respect to temperature and require no hardware or software based linearization. In addition, the optical components measure the temperature at the location that is most relevant for use in obtaining a temperature corrected analyte value. Third, since the illumination and/or detection optical components are employed directly in the temperature measurement, an additional component such as a thermistor is not required, thereby providing for benefits in terms of manufacture and cost of the device. As such, the subject invention represents a significant contribution to the art.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method for determining the concentration of an analyte in a sample of fluid, said method comprising:

contacting said sample with a matrix comprising a signal producing system that produces a colored product on said matrix in an amount proportional to the amount of analyte in said sample;

illuminating a surface of said matrix with an illumination means;

collecting light from said surface with a light detection means to obtain an optical measurement;

obtaining an ambient temperature value proximal said matrix using said light detection means; and determining said analyte concentration in said sample from said optical measurement using an algorithm that employs said ambient temperature value.

2. The method according to claim 1, wherein said collecting comprises collecting reflected light and said optical measurement is a reflectance measurement.

3. The method according to claim 2, wherein said ambient temperature value is obtained at least once at a time prior to, during and/or after obtainment of said reflectance measurement.

4. The method according to claim 1, wherein said illumination means is a light emitting diode.

5. The method according to claim 1, wherein said light detection means is a temperature sensitive light detector.

6. The method according to claim 1, wherein said fluid is a body fluid.

7. The method according to claim 6, wherein said body fluid is whole blood or a fraction thereof.

8. The method according to claim 6, wherein said analyte is glucose.

9. The method according to claim 1, wherein said matrix is a component of a reagent test strip.

10. The method according to claim 9, wherein said contacting comprises applying said sample to a sample application area of said matrix.

11. The method according to claim 10, wherein said surface of said matrix that is illuminated by said illumination means is a surface of said matrix located opposite said sample application area.

12. The method according to claim 1, wherein said collecting step (c) occurs after a predetermined incubation period.

13. The method according to claim 12, wherein said temperature value is obtained during said predetermined incubation period.

14. A method for determining the concentration of a blood analyte in a blood sample, said method comprising:

contacting said blood sample with a first surface of a matrix impregnated with a signal producing system that produces a colored product on a second surface opposite said first surface in an amount proportional to the amount of analyte in said blood sample;

illuminating said second surface of said matrix with at least one light emitting diode;

collecting light reflected from said second surface with a photodetector following a predetermined incubation period to obtain a reflectance measurement;

obtaining at least one ambient temperature value proximal said matrix using said photodetector during said incubation period; and determining said analyte concentration in said blood sample from said reflectance measurement using an algorithm that employs said ambient temperature value.

15. The method according to claim 14, wherein said analyte is glucose.

16. The method according to claim 15, wherein said blood sample is whole blood.

17. An apparatus for measuring a concentration of an analyte in a fluid sample, said apparatus comprising:

a chamber for removably accepting a reagent test strip that includes a porous matrix pad which (i) has a first surface for accepting the sample and a reflective second surface opposite to the first surface, (ii) allows the sample to travel through the pad from the first surface toward the second surface, and (iii) is impregnated with one or more reagents of a signal producing system that reacts with said analyte to cause a change in the reflectance of the second surface;

illumination means for illuminating the second surface of the pad;

light detection means for monitoring intensity of light reflected from the second surface of the pad;

ambient temperature means for obtaining an ambient temperature value proximal said porous matrix pad, wherein said ambient temperature means is said light detection means; and means for calculating the analyte concentration from the intensity of reflected light, wherein said means comprises an algorithm that employs said ambient temperature value, wherein said algorithm is recorded on a computer readable medium component of said apparatus.

18. The apparatus according to claim 17, wherein said apparatus further comprises a means for initiating a predetermined time interval upon measuring a change in intensity of reflected light that is indicative of the arrival of a portion of the sample at the second surface.

19. The apparatus according to claim 17, wherein said illumination means is a light emitting diode.

20. The apparatus according to claim 17, wherein said signal producing system produces a detectable product that is proportional to the amount of glucose in the blood sample.

* * * * *